(12) United States Patent
Gross et al.

(10) Patent No.: US 8,668,745 B2
(45) Date of Patent: Mar. 11, 2014

(54) BRIGHTENING AGENT COMPRISING ACYLPYRIDINIUM COMPOUNDS AND DEFINED ALKALIZING AGENTS

(71) Applicant: Henkel AG & Co. KGaA, Duesseldorf (DE)

(72) Inventors: Wibke Gross, Hueckelhoven (DE); Ralph Nemitz, Juechen (DE); Astrid Kroos, Monheim (DE); Frank Janssen, Cologne (DE); Astrid Kleen, Hamburg (DE); Hartmut Manneck, Barnitz (DE); Katja Guenther, Hilden (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 13/916,734

(22) Filed: Jun. 13, 2013

(65) Prior Publication Data
US 2013/0269721 A1 Oct. 17, 2013

Related U.S. Application Data

(63) Continuation of application No. PCT/EP2011/070624, filed on Nov. 22, 2011.

(30) Foreign Application Priority Data

Dec. 17, 2010 (DE) .......................... 10 2010 063 368

(51) Int. Cl.
*D06L 3/10* (2006.01)
(52) U.S. Cl.
USPC ........................ 8/101; 8/107; 8/109; 8/111

(58) Field of Classification Search
USPC ...................................... 8/101, 107, 109, 111
See application file for complete search history.

(56) References Cited

U.S. PATENT DOCUMENTS

| | | | |
|---|---|---|---|
| 8,034,122 B2 * | 10/2011 | Gross et al. ....................... 8/101 |
| 2011/0047712 A1 | 3/2011 | Gross et al. |
| 2011/0146006 A1 | 6/2011 | Gross et al. |
| 2011/0162671 A1 | 7/2011 | Gross et al. |
| 2011/0232669 A1 * | 9/2011 | Suenger et al. ............... 132/208 |
| 2012/0058071 A1 | 3/2012 | Gross et al. |

FOREIGN PATENT DOCUMENTS

| | | |
|---|---|---|
| DE | 102005059647 A1 | 6/2007 |
| WO | 2009/135700 A1 | 11/2009 |
| WO | 2010/054981 A2 | 5/2010 |

OTHER PUBLICATIONS

STIC Search Report dated Jul. 31, 2013.*
PCT International Search Report (PCT/EP2011/070624) dated May 17, 2013.

* cited by examiner

*Primary Examiner* — Eisa Elhilo
(74) *Attorney, Agent, or Firm* — Ingrassia Fisher & Lorenz, P.C.

(57) ABSTRACT

The invention provides an agent for lightening keratinic fibers, the agent containing in a cosmetic carrier (i) at least one acyl pyridinium derivative of formula (I), (ii) at least one alkalizing agent selected from triethanolamine, 2-amino-2-methylpropan-1-ol, 2-amino-2-methylpropane-1,3-diol, lysine, ornithine and/or an alkalizing agent mixture comprising at least one basic amino acid and at least one alkanolamine, and (iii) at least hydrogen peroxide as an oxidizing agent.

12 Claims, No Drawings

BRIGHTENING AGENT COMPRISING ACYLPYRIDINIUM COMPOUNDS AND DEFINED ALKALIZING AGENTS

CROSS-REFERENCE TO RELATED APPLICATION

This is a continuation of International Application No. PCT/EP2011/070624, filed Nov. 22, 2011, which was published under PCT Article 21(2), which is hereby incorporated in its entirety by reference.

FIELD OF THE INVENTION

The present invention generally relates to agents for lightening keratinic fibers, in particular human hair, containing a special bleach activator.

BACKGROUND OF THE INVENTION

The altering of hair color is an important area of modern cosmetics. Various bleaching agents with varying bleaching capacity are available on the market for the purpose of lightening the natural hair color or for bleaching. The basic principles of bleaching methods are known to the person skilled in the art and can be researched in relevant monographs by, for example, Kh. Schrader, Grundlagen and Rezepturen der Kosmetika, $2^{nd}$ edition, 1989, Dr. Alfred Hüthig Verlag, Heidelberg, or W. Umbach (Ed.), Kosmetik, $2^{nd}$ edition, 1995, Georg Thieme Verlag, Stuttgart, N.Y.

The oxidizing agents contained in bleaching agents have the ability to lighten the hair fiber by means of the oxidative breakdown of the hair's natural pigment, melanin. For a moderate bleaching effect, the use of hydrogen peroxide—preferably with the use of ammonia or other alkalizing agents—is sufficient as an oxidizing agent on its own; for a stronger bleaching effect, a mixture of hydrogen peroxide and peroxodisulfate salts and/or peroxomonosulfate salts is conventionally used. Lightening is, however, also associated with damage to the hair, as not only the natural coloring components of the hair but also the other structural constituents of the hair are damaged by oxidation. Depending on the extent of the damage, it can range from coarse, brittle and tangled hair, through reduced resistance and breaking strength of the hair, to breakage of the hair. Larger amounts of hydrogen peroxide and optionally peroxodisulfates tend to be associated with greater damage to the keratin fiber. Although the bleaching agents hitherto available on the market generally have good lightening capacity, they cannot be regarded as ideal because of the hair damage, long application times and possible skin irritation caused by the high concentrations of oxidizing and alkalizing agents. There is therefore still a need for lightening agents that have a good lightening capacity without at the same time damaging the hair fiber.

Lightening or bleaching agents generally require a basic pH, in particular between pH 8.0 and pH 12. These pH values are necessary to ensure that the external cuticle opens and to allow the active species, in particular hydrogen peroxide, to penetrate into the hair. The basic environment constitutes a further cause of damage to the hair and its structure, however, which likewise gains in importance as the application time increases. The splaying of the external cuticle leads moreover to an unpleasant surface sensitivity of the hair, making it more difficult to comb when wet and dry.

The necessary basic pH value is frequently established using ammonia as the alkalizing agent, as ammonia-containing bleaching agents have additional advantages in terms of lightening capacity. For the user, however, such a lightening agent has the disadvantage that in addition to causing additional damage to the hair, ammonia can also lead to irritation of the eyes or scalp, which can give rise to sensitization or even to allergic reactions. Furthermore, such hair treatment agents have a strong, unpleasant odor, which in the worst-case scenario can also lead to irritation of the nasal mucosa. The production and storage of ammonia-containing lightening agents can moreover be associated with problems in terms of handling ability and stability.

A strengthening of the lightening effect in the bleaching of hair with the aid of a combination of certain acyl pyridinium derivatives and hydrogen peroxide is known from the document WO 2009/135700 A1.

It could not be inferred from the prior art to date that a combination of specific acyl pyridinium derivatives, hydrogen peroxide and specific alkalizing agents not only improves the lightening capacity in comparison to a standard bleach containing hydrogen peroxide, as is already known, but additionally also has an optimal lightening capacity without additional damage to the hair and in particular without additional irritation to the eyes or scalp.

The object of the present invention is to provide an agent which not only lightens the hair more intensely than if hydrogen peroxide is used alone but additionally also has an optimal lightening capacity without additional damage to the hair and in particular without additional irritation to the eyes or scalp. These agents should not have noticeably unpleasant odors, nor should they lead to irritation of the scalp and nasal mucosa.

Furthermore, other desirable features and characteristics of the present invention will become apparent from the subsequent detailed description of the invention and the appended claims, taken in conjunction with this background of the invention.

BRIEF SUMMARY OF THE INVENTION

In an embodiment, an agent for lightening keratinic fibers comprises, in a cosmetically acceptable carrier, (i) at least one acyl pyridinium derivative of formula (I),

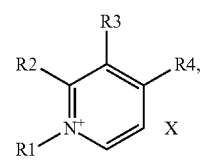

(1)

in which R1 denotes a $C_1$-$C_6$ alkyl group, a $C_2$-$C_6$ alkenyl group, a $C_2$-$C_6$ hydroxyalkyl group, a $C_1$-$C_6$ alkoxy $C_2$-$C_6$ alkyl group, a carboxy $C_2$-$C_6$ alkyl group, an aryl $C_1$-$C_6$ alkyl group, a heteroaryl $C_1$-$C_6$ alkyl group, an aryl group or a heteroaryl group, R2, R3 and R4 each independently of one another denote hydrogen, a $C_1$-$C_6$ alkyl group, a halogen atom or a $C_1$-$C_6$ acyl group, with the proviso that at least one of the residues R2, R3 and R4 denotes a $C_1$-$C_6$ acyl group, $X^-$ denotes a physiologically acceptable anion; (ii) at least one alkalizing agent selected from triethanolamine, 2-amino-2-methylpropan-1-ol, 2-amino-2-methylpropane-1,3-diol, lysine, ornithine and/or an alkalizing agent mixture comprising at least one basic amino acid and at least one alkanolamine; and (iii) at least hydrogen peroxide as an oxidizing agent.

In an embodiment, a packaging unit comprises a plurality of components encompassing at least two containers packaged separately from each other, wherein the packaging unit comprises: a first container C1 containing at least one agent, M1, containing in a cosmetically acceptable carrier at least hydrogen peroxide as an oxidizing agent, and a second container C2 containing at least one agent, M2, containing in a cosmetically acceptable carrier at least one alkalizing agent, selected from triethanolamine, 2-amino-2-methylpropan-1-ol, 2-amino-2-methylpropane-1,3-diol, lysine, ornithine and/or an alkalizing agent mixture comprising at least one basic amino acid and at least one alkanolamine, wherein at least one of the agents M1 and/or M2 contains an acyl pyridinium derivative of formula (I)

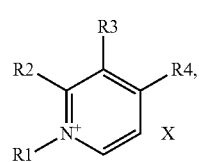

(1)

in which R1 denotes a $C_1$-$C_6$ alkyl group, a $C_2$-$C_6$ alkenyl group, a $C_2$-$C_6$ hydroxyalkyl group, a $C_1$-$C_6$ alkoxy $C_2$-$C_6$ alkyl group, a carboxy $C_2$-$C_6$ alkyl group, an aryl $C_1$-$C_6$ alkyl group, a heteroaryl $C_1$-$C_6$ alkyl group, an aryl group or a heteroaryl group, R2, R3 and R4 each independently of one another denote hydrogen, a $C_1$-$C_6$ alkyl group, a halogen atom or a $C_1$-$C_6$ acyl group, with the proviso that at least one of the residues R2, R3 and R4 denotes a $C_1$-$C_6$ acyl group, X⁻ denotes a physiologically acceptable anion.

In an embodiment, a method for lightening human hair, comprises: (i) preparing a ready-to-use agent by mixing together agents M1 and M2 from a packaging unit comprising a plurality of components wherein the packaging unit comprises: a first container C1 containing at least one agent, M1, containing in a cosmetically acceptable carrier at least hydrogen peroxide as an oxidizing agent, and a second container C2 containing at least one agent, M2, containing in a cosmetically acceptable carrier at least one alkalizing agent, selected from triethanolamine, 2-amino-2-methylpropan-1-ol, 2-amino-2-methylpropane-1,3-diol, lysine, ornithine and/or an alkalizing agent mixture comprising at least one basic amino acid and at least one alkanolamine, wherein at least one of the agents M1 and/or M2 contains an acyl pyridinium derivative of formula (I)

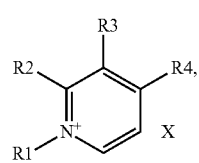

(1)

in which R1 denotes a $C_1$-$C_6$ alkyl group, a $C_2$-$C_6$ alkenyl group, a $C_2$-$C_6$ hydroxyalkyl group, a $C_1$-$C_6$ alkoxy $C_2$-$C_6$ alkyl group, a carboxy $C_2$-$C_6$ alkyl group, an aryl $C_1$-$C_6$ alkyl group, a heteroaryl $C_1$-$C_6$ alkyl group, an aryl group or a heteroaryl group, R2, R3 and R4 each independently of one another denote hydrogen, a $C_1$-$C_6$ alkyl group, a halogen atom or a $C_1$-$C_6$ acyl group, with the proviso that at least one of the residues R2, R3 and R4 denotes a $C_1$-$C_6$ acyl group, X⁻ denotes a physiologically acceptable anion, (ii) applying the ready-to-use agent immediately thereafter to the sections of hair to be lightened, (iii) leaving the agent on the hair sections for a contact time, and (iv) rinsing the agent out of the hair.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

It is known to the person skilled in the art that the best lightening results can generally be obtained using ammonia as the alkalizing agent. Switching to alternative alkalizing agents is normally also associated, however, with a reduction in the bleaching capacity.

It was therefore in no way foreseeable for the person skilled in the art that these formulations, containing a combination of selected alkalizing agents and in particular special mixtures of alkalizing agents with hydrogen peroxide and specific acyl pyridinium compounds, would combine the advantage of high skin compatibility with a good bleaching capacity and that a lightening effect can also be achieved with these special formulations which shows no diminution in comparison to the use of ammonia.

Through the combination of selected alkalizing agents and in particular special mixtures of alkalizing agents with hydrogen peroxide and specific acyl pyridinium compounds, low-odor formulations can be produced which offer good skin compatibility and in terms of irritation to the scalp and nasal mucosa have more advantageous properties than the hitherto known prior art.

The invention thus firstly provides an agent for lightening keratinic fibers, wherein it contains in a cosmetic carrier
(i) at least one acyl pyridinium derivative of formula (I),

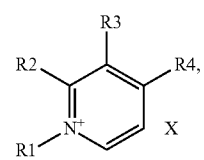

(1)

in which
R1 denotes a $C_1$-$C_6$ alkyl group, a $C_2$-$C_6$ alkenyl group, a $C_2$-$C_6$ hydroxyalkyl group, a $C_1$-$C_6$ alkoxy $C_2$-$C_6$ alkyl group, a carboxy $C_2$-$C_6$ alkyl group, an aryl $C_1$-$C_6$ alkyl group, a heteroaryl $C_1$-$C_6$ alkyl group, an aryl group or a heteroaryl group,
R2, R3 and R4 each independently of one another denote hydrogen, a $C_1$-$C_6$ alkyl group, a halogen atom or a $C_1$-$C_6$ acyl group, with the proviso that at least one of the residues R2, R3 and R4 denotes a $C_1$-$C_6$ acyl group,
X⁻ denotes a physiologically acceptable anion,
(ii) at least one alkalizing agent selected from triethanolamine, 2-amino-2-methylpropan-1-ol, 2-amino-2-methylpropane-1,3-diol, lysine, ornithine and/or an alkalizing agent mixture comprising at least one basic amino acid and at least one alkanolamine, and
(iii) at least hydrogen peroxide as an oxidizing agent.

The term keratinic fibers or keratin fibers is understood here to mean fur, wool, feathers and in particular human hair. Although the agents according to the invention are primarily suitable for lightening keratin fibers, there is nothing in principle to preclude their use in other fields.

The agents according to the invention contain the active ingredients in a cosmetic carrier. The cosmetic carrier is preferably aqueous, alcoholic or aqueous-alcoholic. For the purposes of hair bleaching such carriers are for example creams, emulsions, gels or surfactant-containing foaming solutions, such as for example shampoos, foam aerosols or other preparations that are suitable for use on the hair. An aqueous carrier contains within the meaning of the invention at least 40 wt. %, in particular at least 50 wt. %, of water. Within the meaning of the present invention aqueous-alcoholic carriers are understood to be hydrous compositions containing 3 to 70 wt. % of a $C_1$ to $C_4$ alcohol, in particular ethanol or isopropanol. The agents according to the invention can additionally contain further organic solvents, such as for example methoxybutanol, ethyl diglycol, 1,2-propylene glycol, n-propanol, n-butanol, n-butylene glycol, glycerol, diethylene glycol monoethyl ether, and diethylene glycol mono-n-butyl ether. All water-soluble organic solvents are preferred here.

As the first substantial ingredient, the agents according to the invention contain at least one acyl pyridinium derivative according to formula (I). The following non-limiting examples are cited as substituents of compounds of formula (I): Examples of $C_1$-$C_6$ alkyl residues are the groups —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)CH_2CH_3$, —$C(CH_3)_3$. Examples of a $C_2$-$C_6$ alkenyl group are a prop-2-enyl group (allyl group), a 2-methylprop-2-enyl group, a but-3-enyl group, a but-2-enyl group, a pent-4-enyl group or a pent-3-enyl group, the prop-2-enyl group being preferred. Examples of a $C_2$-$C_6$ hydroxyalkyl group are —$CH_2CH_2OH$, —$CH_2CH_2CH_2OH$, —$CH_2CH(OH)CH_3$ and —$CH_2CH_2CH_2CH_2OH$, the —$CH_2CH_2OH$ group being preferred. Examples of $C_1$-$C_6$ alkoxy $C_2$-$C_6$ alkyl groups are the —$CH_2CH_2OCH_3$, —$CH_2CH_2CH_2OCH_3$, —$CH_2CH_2OCH_2CH_3$, —$CH_2CH_2CH_2OCH_2CH_3$, —$CH_2CH_2OCH(CH_3)_2$, —$CH_2CH_2CH_2OCH(CH_3)_2$ groups. Examples of a carboxy $C_1$-$C_6$ alkyl group are the carboxymethyl group, the 2-carboxyethyl group or the 3-carboxypropyl group. Examples of aryl $C_1$-$C_6$ alkyl groups are the benzyl group and the 2-phenylethyl group. Examples of a heteroaryl $C_1$-$C_6$ alkyl group are the pyridin-2-yl methyl group, the pyridin-3-yl methyl group, the pyridin-4-yl methyl group, the pyrimidin-2-yl methyl group, the pyrrol-1-yl methyl group, the pyrrol-1-yl ethyl group, the pyrazol-1-yl methyl group or the pyrazol-1-yl ethyl group. Examples of an aryl group are the phenyl group, the 1-naphthyl group or the 2-naphthyl group. Examples of a heteroaryl group are the pyridin-2-yl group, the pyridin-3-yl group, the pyridin-4-yl group, the pyrimidin-2-yl group, the pyrrol-1-yl group, the pyrrol-2-yl group, the pyrazol-1-yl group, the pyrazol-3-yl group or the pyrazol-4-yl group. Examples of a $C_1$-$C_6$ acyl group are acetyl (1-oxo-ethyl), 1-oxo-propyl, 1-oxo-butyl, 1-oxo-pentyl, 1-oxo-2,2-dimethylpropyl and 1-oxo-hexyl.

In an embodiment of the present invention, compounds according to formula (I) are preferred in which the residue R1 of the general structure (I) denotes a $C_1$-$C_6$ alkyl group, a $C_2$-$C_6$ alkenyl group or a $C_2$-$C_6$ hydroxyalkyl group. It is preferable according to the invention for the residue R1 to denote a $C_1$-$C_6$ alkyl group, preferably methyl, ethyl, n-propyl or isopropyl, and in particular preferably methyl.

It has been found that acyl pyridinium derivatives according to formula (I) have particularly advantageous properties according to the invention if they bear the acyl group in either the 2- or 4-position on the pyridine ring. Preferred compounds of formula (I) are furthermore compounds in which either the residue R2 or the residue R4 denotes a $C_1$-$C_6$ acyl group, preferably an acetyl group. It is furthermore preferable for one of the residues R2 or R4 to denote an acetyl group, while the other of these residues and the residue R3 each denote hydrogen. A further embodiment of the present invention therefore has the characterizing feature that the agent contains at least one 2-acetyl pyridinium derivative and/or 4-acetyl pyridinium derivative as the acyl pyridinium derivative according to formula (I). Suitable acetyl pyridinium derivatives are in particular the physiologically acceptable salts containing as cation an acetyl pyridinium derivative selected from 4-acetyl-1-methylpyridinium, 4-acetyl-1-allylpyridinium, 4-acetyl-1-(2-hydroxyethyl)pyridinium, 2-acetyl-1-methylpyridinium, 2-acetyl-1-allylpyridinium and 2-acetyl-1-(2-hydroxyethyl)pyridinium.

It is preferable for the anion $X^-$ according to formula (I) to be selected from halide, in particular chloride, bromide and iodide, benzenesulfonate, p-toluenesulfonate, $C_1$-$C_4$ alkylsulfonate, trifluoromethanesulfonate, acetate, trifluoroacetate, perchlorate, ½ sulfate, hydrogen sulfate, tetrafluoroborate, hexafluorophosphate or tetrachlorozincate. It is advantageous according to the invention for the physiologically acceptable anion $X^-$ to denote a halide ion (in particular chloride or bromide), hydrogen sulfate, p-toluenesulfonate, benzenesulfonate or acetate.

In particular, agents are preferred according to the invention which have the characterizing feature that the acyl pyridinium derivative according to formula (I) is selected from at least one compound of selected from the group consisting of 4-acetyl-1-methylpyridinium-p-toluenesulfonate, 4-acetyl-1-methylpyridinium benzenesulfonate, 4-acetyl-1-methylpyridinium hydrogen sulfate, 4-acetyl-1-methylpyridinium acetate, 4-acetyl-1-allylpyridinium-p-toluenesulfonate, 4-acetyl-1-allylpyridinium benzenesulfonate, 4-acetyl-1-allylpyridinium hydrogen sulfate, 4-acetyl-1-allylpyridinium acetate, 2-acetyl-1-methylpyridinium-p-toluenesulfonate, 2-acetyl-1-methylpyridinium benzenesulfonate, 2-acetyl-1-methylpyridinium hydrogen sulfate, 2-acetyl-1-methylpyridinium acetate, 2-acetyl-1-allylpyridinium-p-toluenesulfonate, 2-acetyl-1-allylpyridinium benzenesulfonate, 2-acetyl-1-allylpyridinium hydrogen sulfate and 2-acetyl-1-allylpyridinium acetate. Particularly preferred agents according to the invention have the characterizing feature that as the acyl pyridinium derivative according to formula (I) they contain a compound selected from 4-acetyl-1-methylpyridinium-p-toluenesulfonate and/or 2-acetyl-1-methylpyridinium-p-toluenesulfonate, in particular 4-acetyl-1-methylpyridinium-p-toluenesulfonate.

An embodiment of the present invention has the characterizing feature that the acyl pyridinium derivatives of formula (I) are contained in the agent according to the invention in a proportion by weight from 0.1 to 10 wt. %, in particular from 0.2 to 4 wt. %, and in particular 0.5 to 2 wt. %, relative in each case to the total weight of the agent.

As a further substantial ingredient the agents according to the invention furthermore contain at least one alkalizing agent selected from triethanolamine, 2-amino-2-methylpropan-1-ol, 2-amino-2-methylpropane-1,3-diol, lysine, ornithine and/or an alkalizing agent mixture comprising at least one basic amino acid and at least one alkanolamine.

An amino acid within the meaning of the invention is classed as an organic compound containing in its structure at least one protonizable amino group and at least one —COOH or —$SO_3H$ group. Preferred amino acids are amino carboxylic acids, in particular α-(alpha)-amino carboxylic acids and ω-aminocarboxylic acids, α-aminocarboxylic acids being particularly preferred.

Basic amino acids are understood according to the invention to be amino acids that have an isoelectric point, pI, of greater than 7.0.

Basic α-aminocarboxylic acids contain at least one asymmetrical carbon atom. In the context of the present invention both possible enantiomers can be used equally as a specific compound as or mixtures thereof, in particular as racemates. It is particularly advantageous, however, to use the naturally preferentially occurring isomer forms, conventionally in L-configuration.

The basic amino acids are preferably selected from the group consisting of arginine, lysine, ornithine and histidine, particularly preferably from arginine and lysine.

The alkanolamines for use in the alkalizing agent mixture according to the invention are preferably selected from primary amines having a $C_2$-$C_6$ alkyl parent substance bearing at least one hydroxyl group. Preferred alkanolamines are selected from the group consisting of 2-amino ethan-1-ol (mono ethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropane-1,2-diol, 2-amino-2-methylpropane-1,3-diol. Particularly preferred alkanolamines according to the invention are selected from the group comprising 2-amino ethan-1-ol and 2-amino-2-methylpropan-1-ol.

Preferred agents according to the invention contain an alkalizing agent mixture.

A further embodiment of the first subject-matter of the invention is an agent which has the characterizing feature that as alkalizing agent the agent contains at least one alkalizing agent mixture comprising at least one basic amino acid, selected from arginine, histidine, lysine and ornithine, and at least one alkanolamine, selected from ethanolamine, triethanolamine, 2-amino-2-methylpropan-1-ol and 2-amino-2-methylpropane-1,3-diol.

A preferred embodiment of the first subject-matter of the invention is an agent which has the characterizing feature that as alkalizing agent the agent contains at least one alkalizing agent mixture, selected from the combination of arginine and ethanolamine, the combination of arginine and 2-amino-2-methylpropan-1-ol, the combination of lysine and 2-amino-2-methylpropan-1-ol, and/or the combination of lysine and ethanolamine.

The agent can, moreover, contain further alkalizing agents, in particular inorganic alkalizing agents. Inorganic alkalizing agents for use according to the invention are preferably selected from the group consisting of sodium hydroxide, potassium hydroxide, calcium hydroxide, barium hydroxide, sodium phosphate, potassium phosphate, sodium silicate, sodium metasilicate, potassium silicate, sodium carbonate and potassium carbonate.

As the third substantial constituent the agent according to the invention contains at least hydrogen peroxide as an oxidizing agent. Hydrogen peroxide itself is preferably used as an aqueous solution. Hydrogen peroxide can however also be used in the form of a solid addition compound of hydrogen peroxide with inorganic or organic compounds, such as sodium percarbamide, polyvinyl pyrrolidinone n $H_2O_2$ (n is a positive integer greater than 0), urea peroxide and melamine peroxide.

Hydrogen peroxide is preferably contained in the ready-to-use agent in an amount from 0.1 to 25 wt. %, in particular preferably from 1 to 20 wt. % and particularly preferably from 4.5 to 9 wt. %, calculated in each case against 100% hydrogen peroxide and relative to the total weight of the ready-to-use agent.

Taking account of the aforementioned preferred embodiments, a most specific and expressly preferred embodiment is one in which the agent for lightening keratinic fibers in a cosmetic carrier contains at least one compound selected from the group consisting of 4-acetyl-1-methylpyridinium-p-toluenesulfonate, 4-acetyl-1-methylpyridinium benzenesulfonate, 4-acetyl-1-methylpyridinium hydrogen sulfate, 4-acetyl-1-methylpyridinium acetate, 4-acetyl-1-allylpyridinium-p-toluenesulfonate, 4-acetyl-1-allylpyridinium benzenesulfonate, 4-acetyl-1-allylpyridinium hydrogen sulfate, 4-acetyl-1-allylpyridinium acetate, 2-acetyl-1-methylpyridinium-p-toluenesulfonate, 2-acetyl-1-methylpyridinium benzenesulfonate, 2-acetyl-1-methylpyridinium hydrogen sulfate, 2-acetyl-1-methylpyridinium acetate, 2-acetyl-1-allylpyridinium-p-toluenesulfonate, 2-acetyl-1-allylpyridinium benzenesulfonate, 2-acetyl-1-allylpyridinium hydrogen sulfate and 2-acetyl-1-allylpyridinium acetate as the first component, at least one alkalizing agent mixture comprising at least one basic amino acid, selected from arginine, histidine, lysine and ornithine, and at least one alkanolamine, selected from ethanolamine, triethanolamine, 2-amino-2-methylpropan-1-ol and 2-amino-2-methylpropane-1,3-diol, as the second component, and hydrogen peroxide as the third component.

Combinations of the substantial formulation constituents, relative in each case to the ready-to-use agent, in the following combinations (a) to (m) have proved preferable for achieving the object according to the invention:

Combination (a):
3.0 to 6.0 wt. % of hydrogen peroxide, 0.5 to 4.0 wt. % of 4-acetyl-1-methylpyridinium-p-toluenesulfonate and 0.5 to 15.0 wt. % of triethanolamine.

Combination (b):
3.0 to 6.0 wt. % of hydrogen peroxide, 0.5 to 4.0 wt. % of 4-acetyl-1-methylpyridinium-p-toluenesulfonate and 0.5 to 15.0 wt. % of 2-amino-2-methylpropan-1-ol.

Combination (c):
3.0 to 6.0 wt. % of hydrogen peroxide, 0.5 to 4.0 wt. % of 4-acetyl-1-methylpyridinium-p-toluenesulfonate and 0.5 to 15.0 wt. % of 2-amino-2-methylpropane-1,3-diol.

Combination (d):
3.0 to 6.0 wt. % of hydrogen peroxide, 0.5 to 4.0 wt. % of 4-acetyl-1-methylpyridinium-p-toluenesulfonate and 0.5 to 5.0 wt. % of L-lysine.

Combination (e):
3.0 to 6.0 wt. % of hydrogen peroxide, 0.5 to 4.0 wt. % of 4-acetyl-1-methylpyridinium-p-toluenesulfonate and 0.5 to 5.0 wt. % of L-ornithine.

Combination (f):
3.0 to 6.0 wt. % of hydrogen peroxide, 0.5 to 4.0 wt. % of 4-acetyl-1-methylpyridinium-p-toluenesulfonate, 0.5 to 5.0 wt. % of L-arginine and 0.5 to 5.0 wt. % of L-lysine.

Combination (g):
3.0 to 6.0 wt. % of hydrogen peroxide, 0.5 to 4.0 wt. % of 4-acetyl-1-methylpyridinium-p-toluenesulfonate, 0.5 to 5.0 wt. % of L-arginine, 0.5 to 5.0 wt. % of L-lysine and 0.5 to 5.0 wt. % of L-ornithine.

Combination (h):
3.0 to 6.0 wt. % of hydrogen peroxide, 0.5 to 4.0 wt. % of 4-acetyl-1-methylpyridinium-p-toluenesulfonate, 0.5 to 15.0 wt. % of monoethanolamine and 0.5 to 5.0 wt. % of L-arginine Combination (i):
3.0 to 6.0 wt. % of hydrogen peroxide, 0.5 to 4.0 wt. % of 4-acetyl-1-methylpyridinium-p-toluenesulfonate, 0.5 to 15.0 wt. % of monoethanolamine and 0.5 to 5.0 wt. % of L-lysine.
Combination (j):
3.0 to 6.0 wt. % of hydrogen peroxide, 0.5 to 4.0 wt. % of 4-acetyl-1-methylpyridinium-p-toluenesulfonate, 0.5 to 15.0 wt. % of monoethanolamine and 0.5 to 5.0 wt. % of L-ornithine.
Combination (k):
3.0 to 6.0 wt. % of hydrogen peroxide, 0.5 to 4.0 wt. % of 4-acetyl-1-methylpyridinium-p-toluenesulfonate, 0.5 to 15.0 wt. % of 2-amino-2-methylpropan-1-ol and 0.5 to 5.0 wt. % of L-arginine
Combination (l):
3.0 to 6.0 wt. % of hydrogen peroxide, 0.5 to 4.0 wt. % of 4-acetyl-1-methylpyridinium-p-toluenesulfonate, 0.5 to 15.0 wt. % of 2-amino-2-methylpropan-1-ol and 0.5 to 5.0 wt. % of L-lysine.
Combination (m):
3.0 to 6.0 wt. % of hydrogen peroxide, 0.5 to 4.0 wt. % of 4-acetyl-1-methylpyridinium-p-toluenesulfonate, 0.5 to 15.0 wt. % of 2-amino-2-methylpropan-1-ol and 0.5 to 5.0 wt. % of L-ornithine.

The best results were able to be achieved with formulations containing as alkalizing agents both at least one alkanolamine, in particular monoethanolamine or 2-amino-2-methylpropan-1-ol, and at least one basic amino acid, selected from the group comprising arginine, lysine and/or ornithine. Explicitly most particularly preferred are therefore the combinations containing both an alkanolamine and a basic amino acid in the following concentration ranges. Particularly preferred agents therefore contain as substantial constituents one of combinations (h) to (m).

Bleaching processes on keratin fibers conventionally take place in an alkaline environment. In order to protect the keratin fibers and also the skin as far as possible, it is not desirable to establish too high a pH, however. The pH values within the meaning of the present invention are pH values measured at a temperature of 22° C.

Acidifying agents that are familiar to the person skilled in the art are commonly used for adjusting the pH. Preferred acidifying agents according to the invention are food acids, such as lactic acid, citric acid, acetic acid, malic acid or tartaric acid, dilute mineral acids and salts thereof that are acid-reacting in water, as well as organic phosphonic or sulfonic acids.

To improve the lightening capacity, however, the ready-to-use bleaching agents preferably have an alkaline pH. It is therefore preferable to adjust an agent of the first subject-matter of the invention to an alkaline pH of between 6 and 12, in particular between 9 and 11, immediately before it is applied to the keratinic fibers.

An embodiment of the first subject-matter of the invention is therefore an agent which has the characterizing feature that it has a pH from 7.5 to 12, preferably 8.5 to 11.5, and in particular preferably from 9 to 11.

It has furthermore proved advantageous for the agents to contain at least one stabilizer or complexing agent. Particularly preferred stabilizers are phenacetin, alkali benzoates (sodium benzoate) and salicylic acid.

Also preferred according to the invention is the use of complexing agents. Complexing agents are substances that are capable of complexing metal ions. Preferred complexing agents are chelating agents, in other words substances which form cyclic compounds with metal ions, wherein an individual ligand occupies more than one coordination site on a central atom, i.e. it is at least "bidentate". Common chelating agents which are preferred in the context of the present invention are for example polyoxycarboxylic acids, polyamines, ethylenediaminetetraacetic acid (EDTA), nitrilotriacetic acid (NTA) and hydroxyethane diphosphonic acids or the alkali salts thereof. Complexing polymers, in other words polymers bearing functional groups either in the main chain itself or laterally thereto which can act as ligands and react with suitable metal atoms, generally forming chelate complexes, can also be used according to the invention. The polymer-bound ligands of the metal complexes formed can derive from just one macromolecule or can belong to various polymer chains. Complexing agents that are preferred according to the invention are nitrogen-containing polycarboxylic acids, in particular EDTA, and phosphonates, preferably hydroxyalkane or aminoalkane phosphonates, and in particular 1-hydroxyethane-1,1-diphosphonate (HEDP) or the disodium or tetrasodium salt thereof and/or ethylenediamine tetramethylene phosphonate (EDTMP) or the hexasodium salt thereof and/or diethylenetriamine pentamethylene phosphonate (DTPMP) or the heptasodium or octasodium salt thereof.

According to the invention the agent can be applied to the hair together with a catalyst that additionally activates oxidation of the dye precursors. Such catalysts are for example specific enzymes, iodides, quinones or metal ions. Suitable enzymes for this purpose are for example peroxidases, which can significantly strengthen the action of small amounts of hydrogen peroxide. A use of specific metal ions or complexes can likewise be preferred. $Zn^{2+}$, $Cu^{2+}$ and $Mn^{2+}$ are particularly suitable.

To prevent instabilities due to undesired reactions between the individual ingredients during storage of the agents, it is convenient to bring the ingredients into contact with one another only immediately before application. To this end it is convenient to package the ingredients separately from one another. On the other hand, for stability reasons it can be expedient to store certain ingredients at a neutral or weakly acid pH and to expose them to an alkaline environment only at the time of application. These ingredients include hydrogen peroxide.

It is advantageous in particular to store the alkalizing agent and hydrogen peroxide separately. The acyl pyridinium derivative of formula (I) can be packaged both together with hydrogen peroxide and together with the alkalizing agent according to the invention. It has proved favorable according to the invention, however, for the acyl pyridinium derivative of formula (I) to be packaged together with hydrogen peroxide.

The ready-to-use agent according to the invention is prepared before application by mixing together an alkalizing preparation M2 and an oxidizing preparation M1. It is therefore advantageous to offer both preparations to the user in a set. For that reason a preferred packaging format of the ready-to-use agent is a separate packaging unit in which the agents M1 and M2 are packaged separately from each other.

It can therefore be preferable for agent M1, containing hydrogen peroxide, to have a weakly acid pH. A further embodiment of the present invention therefore has the characterizing feature that agent M1 has a pH from pH 2 to pH 6, preferably from pH 2.5 to pH 4.5.

The present invention therefore also provides a packaging unit comprising a plurality of components (kit of parts), encompassing at least two containers packaged separately from each other,
  a first container C1 containing at least one agent M1, containing in a cosmetically acceptable carrier at least hydrogen peroxide as an oxidizing agent, and a second container C2 containing at least one agent M2, containing in a cosmetically acceptable carrier at least one alkalizing agent, selected from triethanolamine, 2-amino-2-methylpropan-1-ol, 2-amino-2-methylpropane-1,3-diol, lysine, ornithine and/or an alkalizing agent mixture comprising at least one basic amino acid and at least one alkanolamine, wherein at least one of the agents M1 and/or M2 contains an acyl pyridinium derivative of formula (I) according to claim 1.

In a preferred embodiment at least agent M1 contains an acyl pyridinium compound of formula (I).

A container within the context of the present invention is understood to be a casing in the form of an optionally reclosable bottle, a tube, a can, a packet, a sachet or similar casings. There are no restrictions according to the invention on the casing material. The casings are however preferably made from glass or plastic.

It can furthermore be particularly advantageous according to the invention if the cited kit of parts contains at least one further hair treatment agent in a separate container, in particular a conditioning agent preparation or a bleaching powder with peroxodisulfates. The packaging unit can moreover encompass application aids, such as combs, brushes or applicators, personal protective clothing, in particular disposable gloves, and optionally instructions for use.

Ready-to-use agents according to the invention are preferably aqueous, free-flowing preparations. The agents according to the invention can furthermore contain all active ingredients, additives and auxiliary substances known for such preparations. The ready-to-use agents as a mixture of agent M1 and M2 can contain surface-active substances selected from anionic and non-ionic, zwitterionic, amphoteric and cationic surfactants.

Anionic surfactants have the characterizing feature of a water-solubilizing anionic group such as a carboxylate, sulfate, sulfonate or phosphate group and a lipophilic alkyl group having approximately 8 to 30 C atoms. The molecule can additionally contain glycol or polyglycol ether groups, ester, ether and amide groups and hydroxyl groups. Examples of such anionic surfactants, in each case in the form of the sodium, potassium and ammonium and also the mono-, di- and trialkanolammonium salts having 2 to 4 C atoms in the alkanol group, are linear and branched fatty acids having 8 to 30 C atoms (soaps); ether carboxylic acids, in particular of the formula $RO(CH_2CH_2O)_xCH_2COOH$, in which R is a linear alkyl group having 8 to 30 C atoms and x=0 or 1 to 16; acyl sarcosides; acyl taurides; acyl isethionates; sulfosuccinic acid mono- and dialkyl esters and sulfosuccinic acid monoalkyl polyoxyethyl esters; linear alkane sulfonates; linear $\alpha$-olefin sulfonates; sulfonates of unsaturated fatty acids; $\alpha$-sulfofatty acid methyl esters of fatty acids; alkyl sulfates and alkyl ether sulfates, in particular of the formula $RO(CH_2CH_2O)_xSO_3H$, in which R denotes a linear alkyl group having 8 to 30 C atoms and x denotes 0 or a number from 1 to 12; mixtures of surface-active hydroxy sulfonates; sulfated hydroxyalkyl polyethylene and/or hydroxyalkylene propylene glycol ethers; esters of tartaric acid and citric acid with alcohols; alkyl and/or alkenyl ether phosphates of the formula $RO(C_2H_4O)_xP(=O)(OH)(OR')$, in which R denotes an aliphatic, optionally unsaturated hydrocarbon residue having 8 to 30 carbon atoms, R' denotes hydrogen, a residue $(CH_2CH_2O)_yR$, and x and y independently of each other denote a number from 1 to 10; sulfated fatty acid alkylene glycol esters of the formula $RC(O)O(alkO)_nSO_3H$, in which R denotes a linear or branched, aliphatic, saturated and/or unsaturated alkyl residue having 6 to 22 C atoms, alk denotes $CH_2CH_2$, $CHCH_3CH_2$ and/or $CH_2CHCH_3$ and n denotes a number from 0.5 to 5; and monoglyceride sulfates and monoglyceride ether sulfates.

Surface-active compounds classed as zwitterionic surfactants are those bearing at least one quaternary ammonium group and at least one carboxylate, sulfonate or sulfate group in the molecule. Examples of such zwitterionic surfactants are the betaines such as N-alkyl-N,N-dimethylammonium glycinates, N-acyl aminopropyl-N,N-dimethylammonium glycinates and 2-alkyl-3-carboxymethyl-3-hydroxyethyl imidazolines each having 8 to 18 C atoms in the alkyl or acyl group, and cocoacylaminoethyl hydroxyethyl carboxymethyl glycinate. A preferred zwitterionic surfactant is the fatty acid amide derivative known under the INCI name Cocamidopropyl Betaine.

Amphoteric surfactants are understood to be surface-active compounds which in addition to a $C_8$-$C_{24}$ alkyl or acyl group contain at least one free amino group and at least one —COOH or —$SO_3H$ group in the molecule and are capable of forming internal salts. Conventional amphoteric surfactants are N-alkyl glycines, N-alkyl propionic acids, N-alkyl aminobutyric acids, N-alkyl iminodipropionic acids, N-hydroxyethyl-N-alkyl amidopropyl glycines, N-alkyl taurines, N-alkyl sarcosines, 2-alkyl aminopropionic acids and alkyl aminoacetic acids, each having approximately 8 to 24 C atoms in the alkyl group. Amphoteric surfactants by way of example are N-cocoalkyl aminopropionate, cocoacylaminoethyl aminopropionate and $C_{12}$-$C_{18}$ acyl sarcosine.

Non-ionic surfactants and emulsifiers contain as a hydrophilic group a polyol group, a polyalkylene glycol ether group or a combination of a polyol and polyglycol ether group, for example. Such compounds are for example addition products of 1 to 50 mol of ethylene oxide and/or 0 to 5 mol of propylene oxide with linear and branched fatty alcohols having 8 to 30 C atoms, with fatty acids having 8 to 30 C atoms and with alkyl phenols having 8 to 15 C atoms in the alkyl group; addition products of 1 to 50 mol of ethylene oxide and/or 0 to 5 mol of propylene oxide with linear and branched fatty alcohols having 8 to 30 C atoms, with fatty acids having 8 to 30 C atoms and with alkyl phenols having 8 to 15 C atoms in the alkyl group, end-capped with a methyl or $C_2$ to $C_6$ alkyl residue; polyglycerol esters and alkoxylated polyglycerol esters; polyol fatty acid esters; more highly alkoxylated, propoxylated and in particular ethoxylated, mono-, di- and triglycerides having a degree of alkoxylation of greater than 5, such as for example glycerol monolaurate+20 ethylene oxide and glycerol monostearate+20 ethylene oxide; amine oxides; hydroxyl mixed ethers; sorbitan fatty acid esters and addition products of ethylene oxide with sorbitan fatty acid esters such as for example polysorbates and sorbitan monolaurate+20 mol ethylene oxide (EO); sugar fatty acid esters and addition products of ethylene oxide with sugar fatty acid esters; addition products of ethylene oxide with fatty acid alkanol amides and fatty amines; fatty acid-N-alkyl glucamides; alkyl phenols and alkyl phenol alkoxylates having 6 to 21, in particular 6 to 15 carbon atoms in the alkyl chain and 5 to 30 ethylene oxide and/or propylene oxide units; alkyl polyglycosides corresponding to the general formula RO—$(Z)_x$, in which R denotes alkyl, Z denotes sugar and x denotes the number of sugar units.

The non-ionic emulsifiers within the meaning of the invention also include the polymerization products of ethylene oxide and propylene oxide with saturated or unsaturated fatty alcohols; fatty acid esters of polyhydric alcohols with saturated or unsaturated fatty acids; alkyl esters of saturated or unsaturated fatty acids or alkyl phenols and alkoxylates thereof; in particular ethylene glycol ethers of fatty alcohols;

mixed ethylene and propylene glycol ethers with fatty alcohols; fatty acid esters with sorbitan and polyethylene glycol; esters of non-hydroxylated $C_6$-$C_{30}$ alkyl monocarboxylic acids with polyethylene glycol; and addition products of alkyl phenols with ethylene oxide and/or propylene oxide.

Cationic surfactants of the quaternary ammonium compound, esterquat and amidoamine type are preferred according to the invention in ready-to-use agents. Preferred quaternary ammonium compounds are ammonium halides, in particular chlorides and bromides, such as alkyltrimethylammonium chlorides, dialkyldimethylammonium chlorides and trialkylmethylammonium chlorides, as well as the imidazolium compounds known under the INCI names Quaternium-27 and Quaternium-83. Further cationic surfactants which can be used according to the invention are the quaternized protein hydrolysates. Alkylamidoamines are conventionally produced by amidation of natural or synthetic fatty acids and fatty acid cuts with dialkyl amino amines, such as stearamidopropyl dimethylamine. Likewise preferred esterquats are quaternized ester salts of fatty acids with triethanolamine, quaternized ester salts of fatty acids with diethanol alkyl amines and quaternized ester salts of fatty acids with 1,2-dihydroxypropyl dialkylamines. Such products are sold under the trademarks Stepantex, Dehyquart and Armocare, for example. The products Armocare VGH-70, an N,N-bis(2-palmitoyloxyethyl)dimethylammonium chloride, as well as Dehyquart F-75, Dehyquart C-4046, Dehyquart L80 and Dehyquart AU-35 are examples of such esterquats. The cationic surfactants are contained in the agents used according to the invention preferably in amounts from 0.05 to 10 wt. %, relative to the complete agent. Amounts from 0.1 to 5 wt. % are particularly preferred.

In a preferred embodiment anionic, non-ionic, zwitterionic and/or amphoteric surfactants and mixtures thereof can be preferred.

The agents according to the invention just like agents M1 and/or M2 can contain further active ingredients, auxiliary substances and additives. Further active ingredients, auxiliary substances and additives that can be used according to the invention are for example anionic polymers (such as carbomers, copolymers and cross-polymers of acrylic acid, methacrylic acid, maleic acid, itaconic acid and optionally further non-ionic monomers); further cationic polymers (such as Polyquaternium-4, Polyquaternium-10, Polyquaternium-24, Polyquaternium-67, Polyquaternium-72, Polyquaternium-75, Polyquaternium-29, Polyquaternium-6, Polyquaternium-7, Polyquaternium-22); non-ionic polymers (such as vinyl pyrrolidinone/vinyl acrylate copolymers, polyvinyl pyrrolidinone and vinyl pyrrolidinone/vinyl acetate copolymers and polysiloxanes); zwitterionic and amphoteric polymers (such as acrylamidopropyl trimethylammonium chloride/acrylate copolymers and octylacrylamide/methyl methacrylate/tert-butylamino ethyl methacrylate/2-hydroxypropyl methacrylate copolymers); thickening agents (such as agar-agar, guar gum, alginates, xanthan gum, gum arabic, karaya gum, carob seed meal, linseed gums, dextrans, cellulose derivatives, e.g. methyl cellulose, hydroxyalkyl cellulose and carboxymethyl cellulose, starch fractions and derivatives such as amylose, amylopectin and dextrins, clays such as bentonite or fully synthetic hydrocolloids such as for example polyvinyl alcohol); texturizing agents (such as sugars, maleic acid and lactic acid) and consistency modifiers (such as sugar esters, polyol esters or polyol alkyl ethers); protein hydrolysates (in particular elastin, collagen, keratin, milk protein, soy protein and wheat protein hydrolysates, condensation products thereof with fatty acids); perfume oils; conditioning oils; cyclodextrins; defoaming agents such as silicones; dyes and pigments to color the agent; anti-dandruff active ingredients (such as piroctone olamine, zinc omadine and climbazole); light stabilizers (in particular derivatized benzophenones, cinnamic acid derivatives and triazines); active ingredients (such as allantoin, pyrrolidone carboxylic acids, cholesterol and salts thereof); further fats and waxes (such as fatty alcohols, beeswax, montan wax and paraffins); swelling and penetrating substances (such as glycerol, propylene glycol monoethyl ethers, carbonates, hydrogen carbonates, guanidines, ureas and primary, secondary and tertiary phosphates); opacifiers (such as latex, styrene/PVP and styrene/acrylamide copolymers); pearlescent agents (such as ethylene glycol mono- and distearate and PEG-3 distearate); propellants (such as propane-butane mixtures, $N_2O$, dimethyl ether, $CO_2$ and air) and antioxidants.

The person skilled in the art will select these further substances in accordance with the desired properties of the agents. With regard to further optional components and to the amounts of these components used, reference is expressly made to the relevant manuals known to the person skilled in the art, for example Kh. Schrader, Grundlagen and Rezepturen der Kosmetika, $2^{nd}$ Edition, Hüthig Buch Verlag, Heidelberg, 1989.

The agents according to the invention can be provided not only as pure lightening agents, i.e. as bleaching agents, but also as matting lightening agents, which bring about a matting of the keratin fibers at the same time as lightening them, so that the undesirable color shifts towards reddish or orange ranges that frequently occur in bleaching are balanced out by a slight coloring, in particular in cool shades.

Substantive dyes are used as the coloring component for such matting effects. These are dye molecules which attach directly to the substrate and require no oxidative process to develop the color.

In an embodiment of the present invention the ready-to-use agents according to the invention can contain at least one substantive dye. These are dyes which attach directly to the hair and require no oxidative process to develop the color. Substantive dyes are conventionally nitrophenylene diamines, nitroaminophenols, azo dyes, anthraquinones or indophenols. Substantive dyes are each preferably used in an amount from 0.0001 to 5.0 wt. %, preferably 0.001 to 1.5 wt. %, relative in each case to the complete application preparation. The total amount of substantive dyes is preferably at most 1.0 wt. %.

Preferred anionic substantive dyes are the compounds known under the international names or trade names Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, Acid Black 52, bromophenol blue and tetrabromophenol blue. Preferred cationic substantive dyes are cationic triphenylmethane dyes, such as Basic Blue 7, Basic Blue 26, Basic Violet 2 and Basic Violet 14, aromatic systems which are substituted with a quaternary nitrogen group, such as for example Basic Yellow 57, Basic Red 76, Basic Blue 99, Basic Brown 16 and Basic Brown 17, as well as substantive dyes containing a heterocyclic compound having at least one quaternary nitrogen atom, in particular Basic Yellow 87, Basic Orange 31 and Basic Red 51. Cationic substantive dyes which are sold under the Arianor® brand are likewise particularly preferred cationic substantive dyes according to the invention. Non-ionic nitro and quinone dyes and neutral azo dyes in particular are suitable as non-ionic substantive dyes. Preferred non-ionic substantive dyes are the compounds known under the international names or trade names HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, as well as 1,4-diamino-2-nitrobenzene, 2-amino-4-nitrophenol, 1,4-bis-(2-hydroxyethyl)amino-2-nitrobenzene, 3-nitro-4-(2-hydroxyethyl)aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl)amino-4-nitrobenzene, 2-[(4-amino-2-nitrophenyl)amino]benzoic acid, 6-nitro-1,2,3,4-tetrahydroquinoxaline, 2-hydroxy-1,4-naphthoquinone, picramic acid and salts thereof, 2-amino-6-chloro-4-nitrophenol, 4-ethylamino-3-nitrobenzoic acid and 2-chloro-6-ethylamino-4-nitrophenol. Preferred dye combinations according to the invention are those comprising at least the combination of tetrabromophenol blue and Acid Red 92; tetrabromophenol blue and Acid Red 98; tetrabromophenol blue and Acid Red 94; tetrabromophenol blue and Acid Red 87 or tetrabromophenol blue and Acid Red 51.

It is not necessary for the substantive dyes each to be uniform compounds. Instead it is possible for them also to contain small amounts of further components arising from the manufacturing processes for the individual dyes, provided that they do not adversely influence the coloring result or need to be excluded for other, for example toxicological, reasons.

For intense lightening of very dark hair the use of hydrogen peroxide or its addition products with organic or inorganic compounds alone is often not sufficient. In these cases a combination of hydrogen peroxide and persulfates or peroxodisulfates is generally used in commercial bleaching agents. It has been found that the addition of the acyl pyridinium derivatives according to the invention of the general structure (I) and the alkalizing agents according to the invention alone already leads to a marked improvement in the lightening capacity, so as a rule the addition of persulfates can be dispensed with.

Should the consumer have a desire for a very strong bleaching effect, however, it can be preferred in a further embodiment for at least one inorganic persulfate salt or peroxodisulfate salt to be additionally included in the agent for lightening keratinic fibers in addition to hydrogen peroxide, the acyl pyridinium compound of formula (I) and the alkalizing agent mixture according to the invention.

Preferred peroxodisulfate salts are ammonium peroxodisulfate, potassium peroxodisulfate and sodium peroxodisulfate. The peroxodisulfate salts can be included in an amount from 0.1 to 25 wt. %, in particular in an amount from 0.5 to 15 wt. %, relative to the total weight of the ready-to-use agent. These peroxodisulfates are likewise preferably mixed into the agent only immediately before application, to prevent instabilities during storage.

The agents according to the invention are preferably used for lightening and bleaching human hair. Depending on the user's wishes, the entire hair can be bleached or only certain sections of the hair, such as strands for example, which can optionally be treated separately from the rest of the hair, using foils for example.

The invention therefore also provides a method for lightening human hair, wherein
(i) a ready-to-use agent is prepared by mixing together agents M1 and M2 from a packaging unit comprising a plurality of components according to the preceding subject-matter of the invention,
(ii) immediately thereafter this ready-to-use agent is applied to the sections of hair to be lightened,
(iii) left on the hair sections for a contact time,
(iv) and then the agent is rinsed out of the hair.

The contact time here is 5 to 60 min, preferably 30 to 45 min, before the agent is finally rinsed out. The application temperatures can be in a range between 15 and 40° C. After the contact time the remaining agent is removed from the hair by rinsing. There is no need to wash with a shampoo afterwards if a carrier with a high surfactant content was used.

In the context of this subject-matter of the invention the aforementioned statements apply in an analogous manner with the necessary alterations.

The present invention further provides the cosmetic use of an agent of the first subject-matter of the invention for lightening keratin-containing fibers, in particular human hair.

It has been found that through the combination of an acyl pyridinium derivative of formula (I) with an alkalizing agent selected from triethanolamine, 2-amino-2-methylpropan-1-ol, 2-amino-2-methylpropane-1,3-diol, lysine, ornithine and/or an alkalizing agent mixture comprising at least one basic amino acid and at least one alkanolamine, not only can the lightening capacity of bleaching agents be at least maintained, but in addition low-odor formulations are obtained which offer good skin compatibility and in terms of irritation to the scalp and nasal mucosa have more advantageous properties than the hitherto known prior art.

EXAMPLES

TABLE 1

Developer dispersions D1 to D6

| Raw material (wt. %) | D1 | D2 | D3 | D4 | D5 | D6 |
|---|---|---|---|---|---|---|
| Dipicolinic acid | 0.10 | 0.10 | 0.10 | 0.10 | 0.10 | 0.10 |
| Disodium pyrophosphate | 0.03 | 0.03 | 0.03 | 0.03 | 0.03 | 0.03 |
| Turpinal SL | 1.50 | 1.50 | 1.50 | 1.50 | 1.50 | 1.50 |
| Texapon NSO | 2.00 | 2.00 | 2.00 | 2.00 | 2.00 | 2.00 |
| Acrylates copolymer | 4.00 | 4.00 | 4.00 | 4.00 | 4.00 | 4.00 |
| Hydrogen peroxide 50% | 22.40 | 22.40 | 22.40 | 22.40 | 22.40 | 22.40 |
| 4-Acetyl-1-methylpyridinium-p-toluenesulfonate | 2.00 | 1.50 | 3.00 | 3.00 | 3.50 | 3.50 |
| Citric acid or ethanolamine | to pH 2.5 | to pH 3.0 | to pH 4.0 | to pH 2.0 | to pH 3.0 | to pH 4.0 |
| Water | to 100 | | | | | |

TABLE 2

Bleaching creams B1 to B7

| Raw material (wt. %) | B1 | B2 | B3 | B4 | B5 | B6 | B7 |
|---|---|---|---|---|---|---|---|
| Cetearyl alcohol | 12.00 | 12.00 | 12.00 | 12.00 | 12.00 | 12.00 | 12.00 |
| Cocoalkyl alcohol | 2.40 | 2.40 | 2.40 | 2.40 | 2.40 | 2.40 | 2.40 |
| Texapon NSO | 26.50 | 26.50 | 26.50 | 26.50 | 26.50 | 26.50 | 26.50 |
| Stabylen 30 | 0.10 | 0.10 | 0.10 | 0.10 | 0.10 | 0.10 | 0.10 |
| Dioctyl ether | 2.40 | 2.40 | 2.40 | 2.40 | 2.40 | 2.40 | 2.40 |
| Turpinal SL | 0.20 | 0.20 | 0.20 | 0.20 | 0.20 | 0.20 | 0.20 |
| Sodium silicate 40/42 | 0.50 | 0.50 | 0.50 | 0.50 | 0.50 | 0.50 | 0.50 |
| Ascorbic acid | 0.20 | 0.20 | 0.20 | 0.20 | 0.20 | 0.20 | 0.20 |
| Ammonia | 3.50 | — | — | — | — | — | — |
| 2-Amino-2-methylpropan-1-ol | — | 5.00 | — | 5.00 | 5.00 | 5.00 | 5.00 |
| Monoethanolamine | — | — | — | — | — | — | — |
| L-Arginine | — | — | — | 1.00 | — | 1.00 | — |
| L-Lysine | — | — | 5.00 | — | 1.00 | 0.50 | — |
| L-Ornithine | — | — | — | — | — | — | 1.00 |
| Water | to 100 | | | | | | |

TABLE 3

Bleaching Creams B8 to B14

| Raw material (wt. %) | B8 | B9 | B10 | B11 | B12 | B13 | B14 |
|---|---|---|---|---|---|---|---|
| Cetearyl alcohol | 12.00 | 12.00 | 12.00 | 12.00 | 12.00 | 12.00 | 12.00 |
| Cocoalkyl alcohol | 2.40 | 2.40 | 2.40 | 2.40 | 2.40 | 2.40 | 2.40 |
| Texapon NSO | 26.50 | 26.50 | 26.50 | 26.50 | 26.50 | 26.50 | 26.50 |
| Stabylen 30 | 0.10 | 0.10 | 0.10 | 0.10 | 0.10 | 0.10 | 0.10 |
| Dioctyl ether | 2.40 | 2.40 | 2.40 | 2.40 | 2.40 | 2.40 | 2.40 |
| Turpinal SL | 0.20 | 0.20 | 0.20 | 0.20 | 0.20 | 0.20 | 0.20 |
| Sodium silicate 40/42 | 0.50 | 0.50 | 0.50 | 0.50 | 0.50 | 0.50 | 0.50 |
| Ascorbic acid | 0.20 | 0.20 | 0.20 | 0.20 | 0.20 | 0.20 | 0.20 |
| 2-Amino-2-methylpropan-1-ol | — | — | — | — | — | 2.50 | 2.50 |
| Monoethanolamine | 5.00 | 5.00 | 5.00 | 5.00 | 5.00 | 2.50 | 2.50 |
| L-Arginine | 1.00 | 0.50 | — | 1.50 | 1.00 | 1.00 | 1.00 |
| L-Lysine | — | 0.50 | 1.00 | — | — | 0.50 | 0.50 |
| L-Ornithine | — | — | — | — | 0.50 | — | — |
| Water | | | | to 100 | | | |

Commercial products used:

Stabylen 30 INCI name: Acrylates/Vinyl Isodecanoate Crosspolymer (Sigma)

Texapon NSO approx. 28% active substance; INCI name: Sodium Laureth Sulfate (Cognis)

Turpinal SL approx. 60% active substance; INCI name: Etidronic Acid (Thermophos)

The developer dispersions D1 to D6 are each mixed with one of the bleaching creams B1 to B14 in a 1:1 weight ratio to form a freshly prepared application preparation. These application preparations have a pH of approximately 9 to 11. The application preparations with bleaching cream B1 are not according to the invention.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. An agent for lightening keratinic fibers, wherein the agent comprises, in a cosmetically acceptable carrier,
    (i) at least one acyl pyridinium derivative of formula (I),

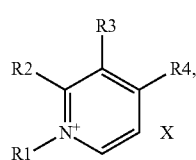

(I)

in which
    R1 denotes a $C_1$-$C_6$ alkyl group, a $C_2$-$C_6$ alkenyl group, a $C_2$-$C_6$ hydroxyalkyl group, a $C_1$-$C_6$ alkoxy $C_2$-$C_6$ alkyl group, a carboxy $C_2$-$C_6$ alkyl group, an aryl $C_1$-$C_6$ alkyl group, a heteroaryl $C_1$-$C_6$ alkyl group, an aryl group or a heteroaryl group, R2, R3 and R4 each independently of one another denote hydrogen, a $C_1$-$C_6$ alkyl group, a halogen atom or a $C_1$-$C_6$ acyl group, with the proviso that at least one of the residues R2, R3 and R4 denotes a $C_1$-$C_6$ acyl group, X$^-$ denotes a physiologically acceptable anion,
    (ii) at least one alkalizing agent, wherein the alkalizing agent consists of one or more amino acid and one or more alkanolamine, and
    (iii) at least hydrogen peroxide as an oxidizing agent.

2. The agent of claim 1, wherein the agent comprises at least one acyl pyridinium derivative of formula (I), selected from at least one compound of the group consisting of 4-acetyl-1-methylpyridinium-p-toluenesulfonate, 4-acetyl-1-methylpyridinium benzenesulfonate, 4-acetyl-1-methylpyridinium hydrogen sulfate, 4-acetyl-1-methylpyridinium acetate, 4-acetyl-1-allylpyridinium-p-toluenesulfonate, 4-acetyl-1-allylpyridinium benzenesulfonate, 4-acetyl-1-allylpyridinium hydrogen sulfate, 4-acetyl-1-allylpyridinium acetate, 2-acetyl-1-methylpyridinium-p-toluenesulfonate, 2-acetyl-1-methylpyridinium benzenesulfonate, 2-acetyl-1-methylpyridinium hydrogen sulfate, 2-acetyl-1-methylpyridinium acetate, 2-acetyl-1-allylpyridinium-p-toluenesulfonate, 2-acetyl-1-allylpyridinium benzenesulfonate, 2-acetyl-1-allylpyridinium hydrogen sulfate and 2-acetyl-1-allylpyridinium acetate.

3. The agent of claim 2, wherein the at least one acyl pyridinium derivative of formula (I) is 4-acetyl-1-methylpyridinium-p-toluenesulfonate.

4. The agent of claim 1, wherein the acyl pyridinium derivatives of formula (I) are included in a proportion by weight from 0.1 to 10 wt. %, relative to the total weight of the agent.

5. The agent of claim 1, wherein the proportion by weight is 0.2 to 4 wt. %, relative to the total weight of the agent.

6. The agent of claim 1, wherein as alkalizing agent, the agent consists of one basic amino acid and one alkanolamine.

7. The agent of claim 1, wherein as alkalizing agent, the basic amino acid is selected from the group consisting of arginine, histidine, lysine and ornithine, and the alkanolamine is selected from the group consisting of ethanolamine, triethanolamine, 2-amino-2-methylpropan-1-ol and 2-amino-2-methylpropane-1,3-diol.

8. The agent according to one of claims 1 to 5, wherein as alkalizing agent the agent contains at least one alkalizing agent mixture, selected from the combination of arginine and ethanolamine, the combination of arginine and 2-amino-2-methylpropan-1-ol, the combination of lysine and 2-amino-2-methylpropan-1-ol, and/or the combination of lysine and ethanolamine.

9. The agent of claim 1, wherein the agent has a pH from 7.5 to 12.

10. The agent of claim 9, wherein the pH is 8.5 to 11.

11. A packaging unit comprising a plurality of components encompassing at least two containers packaged separately from each other, wherein the packaging unit comprises:
    a first container C1 containing at least one agent, M1, containing in a cosmetically acceptable carrier at least hydrogen peroxide as an oxidizing agent, and
    a second container C2 containing at least one agent, M2, containing in a cosmetically acceptable carrier at least one alkalizing agent, wherein the alkalizing agent consists of one or more basic amino acids and one or more alkanolamines,
    wherein at least one of the agents M1 and/or M2 contains an acyl pyridinium derivative of formula (I)

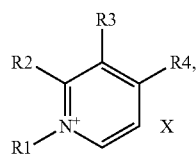

(I)

in which
- R1 denotes a $C_1$-$C_6$ alkyl group, a $C_2$-$C_6$ alkenyl group, a $C_2$-$C_6$ hydroxyalkyl group, a $C_1$-$C_6$ alkoxy $C_2$-$C_6$ alkyl group, a carboxy $C_2$-$C_6$ alkyl group, an aryl $C_1$-$C_6$ alkyl group, a heteroaryl $C_1$-$C_6$ alkyl group, an aryl group or a heteroaryl group,
- R2, R3 and R4 each independently of one another denote hydrogen, a $C_1$-$C_6$ alkyl group, a halogen atom or a $C_1$-$C_6$ acyl group, with the proviso that at least one of the residues R2, R3 and R4 denotes a $C_1$-$C_6$ acyl group,
- $X^-$ denotes a physiologically acceptable anion.

12. A method for lightening human hair, comprising
  (i) preparing a ready-to-use agent by mixing together agents M1 and M2 from a packaging unit comprising a plurality of components wherein the packaging unit comprises:
  a first container C1 containing at least one agent, M1, containing in a cosmetically acceptable carrier at least hydrogen peroxide as an oxidizing agent, and
  a second container C2 containing at least one agent, M2, containing in a cosmetically acceptable carrier at least one alkalizing agent, wherein the alkalizing agent consists of one or more basic amino acids and one or more alkanolamines,
  wherein at least one of the agents M1 and/or M2 contains an acyl pyridinium derivative of formula (I)

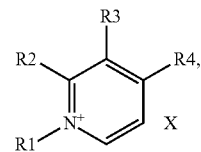

(I)

in which
R1 denotes a $C_1$-$C_6$ alkyl group, a $C_2$-$C_6$ alkenyl group, a $C_2$-$C_6$ hydroxyalkyl group, a $C_1$-$C_6$ alkoxy $C_2$-$C_6$ alkyl group, a carboxy $C_2$-$C_6$ alkyl group, an aryl $C_1$-$C_6$ alkyl group, a heteroaryl $C_1$-$C_6$ alkyl group, an aryl group or a heteroaryl group,
R2, R3 and R4 each independently of one another denote hydrogen, a $C_1$-$C_6$ alkyl group, a halogen atom or a $C_1$-$C_6$ acyl group, with the proviso that at least one of the residues R2, R3 and R4 denotes a $C_1$-$C_6$ acyl group,
$X^-$ denotes a physiologically acceptable anion,
  (ii) applying the ready-to-use agent immediately thereafter to the sections of hair to be lightened,
  (iii) leaving the agent on the hair sections for a contact time, and
  (iv) rinsing the agent out of the hair.

* * * * *